(12) United States Patent
Kanazirev et al.

(10) Patent No.: US 8,940,957 B2
(45) Date of Patent: Jan. 27, 2015

(54) METHOD FOR REMOVAL OF HETEROCYCLIC SULFUR USING METALLIC COPPER

(75) Inventors: Vladislav Ivanov Kanazirev, Arlington Heights, IL (US); Stephen Caskey, Franklin, WI (US); Thomas Traynor, Vernon Hills, IL (US); Dante Simonetti, Palatine, IL (US)

(73) Assignee: UOP LLC, Des Plaines, IL (US)

(*) Notice: Subject to any disclaimer, the term of this patent is extended or adjusted under 35 U.S.C. 154(b) by 203 days.

(21) Appl. No.: 13/367,235

(22) Filed: Feb. 6, 2012

(65) Prior Publication Data

US 2013/0204063 A1 Aug. 8, 2013

(51) Int. Cl.
*C10G 29/04* (2006.01)

(52) U.S. Cl.
USPC ........... 585/823; 585/820; 208/299; 208/296; 208/91; 208/246; 208/247

(58) Field of Classification Search
USPC ................... 585/823, 824; 208/91, 299, 296; 210/660; 95/135
See application file for complete search history.

(56) References Cited

U.S. PATENT DOCUMENTS

| 4,446,005 | A | * | 5/1984 | Eberly et al. | 208/91 |
|---|---|---|---|---|---|
| 4,594,145 | A | * | 6/1986 | Roarty | 208/79 |
| 2003/0106841 | A1 | | 6/2003 | Zong et al. | |
| 2004/0129607 | A1 | * | 7/2004 | Slater et al. | 208/247 |
| 2004/0200758 | A1 | | 10/2004 | Yang et al. | |
| 2007/0098611 | A1 | * | 5/2007 | Yang | 423/213.2 |
| 2010/0012578 | A1 | | 1/2010 | Kanazirev et al. | |
| 2010/0219103 | A1 | | 9/2010 | Reesink | |
| 2010/0300935 | A1 | * | 12/2010 | Nicolaos et al. | 208/91 |

FOREIGN PATENT DOCUMENTS

| CN | 1935948 | A | 3/2007 |
|---|---|---|---|
| GB | 644240 | A | 10/1950 |
| WO | 02053684 | A1 | 7/2002 |

* cited by examiner

*Primary Examiner* — Tam M Nguyen

(57) ABSTRACT

A method of removing heterocyclic sulfide impurities from a fluid stream is presented. The method comprises contacting the fluid stream with a sorbent comprising metallic copper.

20 Claims, No Drawings

METHOD FOR REMOVAL OF HETEROCYCLIC SULFUR USING METALLIC COPPER

FIELD OF THE INVENTION

The disclosure relates in general to the removal of contaminants from hydrocarbon liquids and gases. In certain embodiments, the disclosure relates to the use of a copper-based sorbent to remove heterocyclic sulfides from hydrocarbon streams. In certain embodiments, the disclosure relates to the use of a sorbent comprising supported metallic copper to remove heterocyclic sulfides from hydrocarbon streams.

BACKGROUND OF THE INVENTION

The removal of sulfur compounds from gas and liquid streams is an important process in the hydrocarbon industry. Hydrogen sulfide, a common sulfur-based contaminant, can be removed by supported copper oxide adsorbents known in the prior art. Other sulfur-containing contaminants are, however, more difficult to remove. For example, heterocyclic sulfides, such as thiophene, cannot be effectively removed by prior art copper oxide adsorbents. Nor can heterocyclic sulfides be removed by distillation because they co-boil with desirable hydrocarbons, such as benzene.

Modified zeolites and metal oxides, such as alumina, are known in the prior art to remove heterocyclic sulfides by adsorption. However, in the case of acidic zeolites, the acidity of the zeolite support results in discoloration of the main stream and the shifting of the boiling range of the feed hydrocarbon fraction. In addition, silver exchanged zeolites have low loading capacities and deactivate easily due to changes in the oxidation state of the silver active sites. Finally, $Cu^+$ exchanged zeolites have poor long term stability.

Copper-based adsorbents, including those derived from copper carbonate, are widely used in the hydrocarbon industry to remove contaminants by chemisorption. Copper-based adsorbents, however, are not effective in heterocyclic removal. Accordingly, it would be an advance in the state of the art to provide a copper-based material, and method of using same, for removing heterocyclic sulfur compounds from a hydrocarbon stream via chemisorption.

SUMMARY OF THE INVENTION

A method of removing heterocyclic sulfide impurities from a fluid stream is presented. The method comprises contacting the fluid stream with a sorbent comprising metallic copper.

DETAILED DESCRIPTION OF PREFERRED EMBODIMENTS

The invention is described in preferred embodiments in the following description. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The terms sorbent, adsorbent, and absorbent as used herein refer to the ability of a material to take in or soak up liquid or gas components on the surface thereof or to assimilate such components into the body thereof, whether by chemisorption (i.e., scavenging) or filtering (by way of a molecular sieve).

Applicants' sorbent comprises an active copper phase disposed within a support material. In one embodiment, the active copper phase comprises metallic copper. The metallic copper is capable of reacting with the sulfur atom on the heterocyclic sulfide, such as thiophene (1), at elevated temperatures, thereby scavenging the sulfide from a hydrocarbon stream.

(1)

In one embodiment, substantially all copper in Applicants sorbent is at an oxidation level of +0. In this embodiment, the active copper phase comprises no or substantially no cuprous oxide ($Cu_2O$), and no or substantially no cupric oxide (CuO).

In various embodiments, the support material is a metal oxide selected from the group consisting of alumina, silica, silica-aluminas, silicates, aluminates, silico-aluminates such as zeolites, titania, zirconia, hematite, ceria, magnesium oxide, and tungsten oxide. In one embodiment, the support material is alumina. In some embodiments, the support material is carbon or activated carbon. In certain embodiments, Applicants' sorbent does not comprise a binder.

In various embodiments, the alumina support material is present in the form of transition alumina, which comprises a mixture of poorly crystalline alumina phases such as "rho," "chi" and "pseudo gamma" aluminas which are capable of quick rehydration and can retain substantial amounts of water in a reactive form. An aluminum hydroxide $Al(OH)_3$, such as gibbsite, is a source for preparation of transition alumina. The prior art industrial process for production of transition alumina includes milling gibbsite to 1-20 microns particle size followed by flash calcination for a short contact time as described in the patent literature such as in U.S. Pat. No. 2,915,365. Amorphous aluminum hydroxide and other naturally found mineral crystalline hydroxides, e.g., Bayerite and Nordstrandite or monoxide hydroxides, AlOOH, such as Boehmite and Diaspore can be also used as a source of transition alumina. In certain embodiments, the BET surface area of this transition alumina material is about 300 $m^2/g$ and the average pore diameter is about 30 angstroms as determined by nitrogen adsorption, resulting in a porous sorbent.

In various embodiments, a solid oxysalt of a transition metal is used as a starting component of the sorbent. "Oxysalt," by definition, refers to any salt of an oxyacid. Sometimes this definition is broadened to "a salt containing oxygen as well as a given anion." FeOCl, for example, is regarded as an oxysalt according this definition.

In certain embodiments, the oxysalt comprises one or more copper carbonates. Basic copper carbonates, such as $Cu_2CO_3(OH)_2$, can be produced by precipitation of copper salts, such as $Cu(NO)_3$, $CuSO_4$ and $CuCl_2$, with sodium carbonate. In one embodiment, a synthetic form of malachite, a basic copper carbonate, produced by Phibro Tech, Ridgefield Park, N.J., is used as a component of the sorbent.

Depending on the conditions used, and especially on washing the resulting precipitate, the final material may contain some residual product from the precipitation process. In the case of the $CuCl_2$ raw material, sodium chloride is a side product of the precipitation process. It has been determined that a commercially available basic copper carbonate comprising both residual chloride and sodium, exhibited lower stability towards heating and improved resistance towards reduction than other commercial basic copper carbonates that were practically chloride-free.

In one embodiment, the size of the basic copper carbonate particles is approximately in the range of that of the transition alumina, namely 1-20 microns. In other embodiments, the sorbent comprises the oxysalt Azurite, $Cu_3(CO_3)_2(OH)_2$. In other embodiments, the sorbent comprises an oxysalt of copper, nickel, iron, manganese, cobalt, zinc or a mixture thereof.

In one embodiment, the sorbent is produced by conodulizing basic copper carbonate with alumina followed by curing and activation. In various embodiments, the nodulizing, or agglomeration, is performed in a pan or a drum. The materials are agitated by the oscillating or rotating motion of the nodulizer while spraying with water to form beads. In one embodiment, the beads are cured at about 60° C. and dried in a moving bed activator at a temperature at or below about 175° C. In other embodiments, the sorbent beads are formed by extrusion.

In one embodiment, the sorbent beads are calcinated by heating to between about 350° C. to about 450° C. The heat decomposes the copper carbonate to produce cupric oxide (CuO). In one embodiment, the copper carbonate is fully decomposed to CuO (i.e., there is no or substantially no copper carbonate in the sorbent bead after calcination).

The cupric oxide-containing sorbent is exposed to a reducing environment to form metallic copper. In various embodiments, the reducing environment comprises hydrogen gas ($H_2$), carbon monoxide gas (CO), methane ($CH_4$), or a combination thereof. In various embodiments, the reduction occurs at between about 100° C. to about 210° C., depending on the reducing agent and the exposure time. In various embodiments, the reduction occurs at between about 120° C. to about 190° C. The cupric oxide, with an oxidation state of +2, is first reduced to cuprous oxide, with an oxidation state of +1, and finally to metallic copper, with an oxidation state of +0. In certain embodiments, the conversion of CuO to metallic copper is complete, leaving no or substantially no CuO or $Cu_2O$ in the final sorbent.

In various embodiments, and depending on the application, the sorbent comprises about 5 mass percent copper to about 95 mass percent copper, calculated as CuO on a volatile-free basis. In one embodiment, the sorbent comprises between about 25 mass percent and about 50 mass percent copper, calculated as CuO on a volatile-free basis. In one embodiment, the sorbent comprises about 32 mass percent copper, calculated as CuO on a volatile-free basis. In one embodiment, the sorbent comprises about 68 mass percent copper, calculated as CuO on a volatile-free basis.

In certain embodiments, the sorbent has a diameter (for spherical beads) or maximum width (for irregular shaped beads) of about 1 mm to about 10 mm. In certain embodiments, the sorbent has a diameter or maximum width of about 2 mm to about 6 mm.

In various embodiments, the sorbent is porous (i.e., have a plurality of pores and voids extending therethrough).

The metallic copper-containing sorbent is placed in contact with a flowing hydrocarbon liquid or gas stream, which contains heterocyclic sulfides, at a temperature of about 110° C. to about 200° C.

The following Example is presented to further illustrate to persons skilled in the art how to make and use the invention. This Example is not intended as a limitation, however, upon the scope of Applicant's invention.

EXAMPLE

A mixture of a copper oxysalt and a support material is provided. In one embodiment, the copper oxysalt is basic copper carbonate, $Cu_2(OH)_2CO_3$ and the support material is alumina powder capable of rehydration. In different embodiments, the copper content of the mixture, calculated as CuO on a volatile-free basis, is between about 5 mass percent and about 95 mass percent.

Green sorbent beads are formed from the mixture. As used herein, "green sorbent beads" refer to beads containing the copper oxysalt before reduction to metallic copper and "activated sorbent beads" refer to beads where at least a portion of the copper oxysalt has been fully reduced to metallic copper. In one embodiment, the beads are formed by nodulizing the mixture in a rotating pan nodulizer while spraying with a liquid. In one embodiment, the liquid comprises water.

In another embodiment, the green sorbent beads are formed by agglomeration. In yet another embodiment, the green sorbent beads are formed by extrusion. Those skilled in the art will appreciate that other methods may be performed to form regular- or irregular-shaped beads that fall within the scope of Applicants' invention.

The green sorbent beads are cured and dried. In one embodiment, the curing occurs at about 60° C. In one embodiment, the beads are dried in a moving bed activator at temperatures at or below 175° C.

The copper in the sorbent beads is decomposed to CuO. In one embodiment, the decomposition occurs in an atmosphere of helium, air, nitrogen gas, or a combination thereof. In one embodiment, the decomposition occurs at about 400° C. In certain embodiments, the decomposition to CuO in the sorbent beads is complete (i.e., all or substantially all copper carbonate is decomposed to CuO).

The CuO (oxidation level +2) in the sorbent beads is reduced to metallic copper (Cu, oxidation level +0) by exposure to a reducing environment. In different embodiments, the reducing environment comprises an atmosphere of hydrogen, carbon monoxide, natural gas, methane, or a combination thereof. In various embodiments, the reduction takes place at a temperature of about 120° C. to about 190° C. In certain embodiments, the sorbent comprises no CuO (i.e., all or substantially all CuO is reduced to Cu). In certain embodiments, the reduction is monitored by x-ray detection or color sensors.

In certain embodiments, the cupric oxide (CuO) is reduced to cuprous oxide ($Cu_2O$) and finally to metallic copper. In certain embodiments, the sorbent comprises no $Cu_2O$ (i.e., all or substantially all $Cu_2O$ is reduced to Cu). In certain embodiments, the sorbent comprises no copper oxide (i.e., all or substantially all the copper in the copper carbonate is reduced to metallic copper). In certain embodiments, the copper carbonate is directly reduced to metallic copper without being converted to an intermediate oxide (i.e., CuO, $Cu_2O$) by reaction (1).

$$Cu_2(OH)_2CO_3 + 2H_2 \rightarrow 2Cu + 3H_2O + CO_2 \tag{1}$$

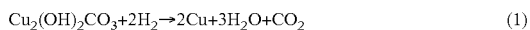

The sorbent is placed in a hydrocarbon fluid (i.e., liquid or gas) stream containing sulfide impurities. In one embodiment, the hydrocarbon stream comprises heterocyclic sulfide impurities, such as without limitation thiophene. In one embodiment, the hydrocarbon stream comprises heterocyclic sulfides and hydrogen sulfide. In one embodiment, the hydrocarbon stream comprises an aromatic compound, such as without limitation benzene. In one embodiment, the hydrocarbon stream comprises an aliphatic compound, such as without limitation heptane. In one embodiment, the temperature of the stream is between about 110° C. to about 200° C. In one embodiment, the temperature of the stream is about 150° C. In one embodiment, the temperature of the stream is about 175° C. In one embodiment, the temperature of the stream is about 200° C.

The described features, structures, or characteristics of the invention may be combined in any suitable manner in one or more embodiments. In the above description, numerous specific details are recited to provide a thorough understanding of embodiments of the invention. One skilled in the relevant art will recognize, however, that the invention may be practiced without one or more of the specific details, or with other methods, components, materials, and an forth. In other instances, well-known structures, materials, or operations are not shown or described in detail to avoid obscuring aspects of the invention. In other words, the present invention may be embodied in other specific forms without departing from its spirit or essential characteristics. The described implementations are to be considered in all respects only as illustrative and not restrictive. The scope of the invention should, therefore, be determined not with reference to the above description, but instead should be determined with reference to the pending claims along with their full scope or equivalents, and all changes which come within the meaning and range of equivalency of the claims are to be embraced within their full scope.

What is claimed is:

1. A method of removing heterocyclic sulfides from a fluid stream, consisting of contacting said fluid stream with a sorbent consisting of metallic copper disposed within a support.

2. The method of claim 1, wherein said sorbent does not comprise a binder.

3. The method of claim 1, wherein said sorbent comprises no copper oxide.

4. The method of claim 1, wherein said sorbent comprises no CuO.

5. The method of claim 4, wherein said sorbent comprises no $Cu_2O$.

6. The method of claim 4, wherein said sorbent further comprises a support material.

7. The method of claim 6, wherein said support material is selected from the group consisting of alumina, silica, silica-aluminas, silicates, aluminates, silico-aluminates, zeolites, titania, zirconia, hematite, ceria, magnesium oxide, and tungsten oxide.

8. The method of claim 6, wherein said support material comprises a transition alumina formed by the flash calcination of gibbsite.

9. The method of claim 8, wherein said sorbent comprises between about 5 mass percent copper to about 95 mass percent copper.

10. The method of claim 9, wherein said sorbent comprises between about 25 mass percent and about 50 mass percent copper.

11. The method of claim 9, wherein said sorbent comprises about 68 mass percent copper.

12. The method of claim 1 wherein said fluid stream is at a temperature from about 110° C. to about 200° C.

13. The method of claim 1, wherein said heterocyclic sulfides comprises thiophene.

14. The method of claim 1, wherein said fluid stream comprises an aromatic compound.

15. The method of claim 14, wherein said aromatic compound comprises benzene.

16. The method of claim 1, wherein said fluid stream comprises an aliphatic compound.

17. The method of claim 16, wherein said aliphatic compound comprises heptane.

18. The method of claim 1, wherein said sorbent is porous.

19. The method of claim 18, wherein said sorbent has a diameter (or maximum width) of between about 1 mm to about 10 mm.

20. The method of claim 19, wherein said sorbent has a diameter (or maximum width) of between about 2 mm to 6 mm.

* * * * *